United States Patent
McCambridge et al.

(10) Patent No.: US 7,467,754 B2
(45) Date of Patent: Dec. 23, 2008

(54) METHOD AND APPARATUS FOR COMMINUTION OF BIOLOGICAL SPECIMENS

(75) Inventors: James E. McCambridge, Polo, IL (US); Scott A. Melton, Erie, IL (US); Carl Salavka, Sudbury, MA (US); Terri Stripling, Greenfield Ctr., NY (US); Jeff Karker, Cazenovia, NY (US); Thomas M. Eden, III, Birmingham, AL (US)

(73) Assignees: Wahl Clipper Corporation, Sterling, IL (US); Drugrisk Solutions, LLC, Schuylerville, NY (US)

( * ) Notice: Subject to any disclaimer, the term of this patent is extended or adjusted under 35 U.S.C. 154(b) by 49 days.

(21) Appl. No.: 10/849,701

(22) Filed: May 20, 2004

(65) Prior Publication Data

US 2005/0258285 A1 Nov. 24, 2005

(51) Int. Cl.
*A47J 19/06* (2006.01)
*B02C 11/00* (2006.01)
*B09B 3/00* (2006.01)

(52) U.S. Cl. .................... 241/2; 241/169.1; 241/169.2

(58) Field of Classification Search .............. 241/89.4, 241/169, 169.1, DIG. 27, 2, 169.2
See application file for complete search history.

(56) References Cited

U.S. PATENT DOCUMENTS

| | | | | |
|---|---|---|---|---|
| 2,022,151 A | * | 11/1935 | Riddle | 241/89.4 |
| 3,738,596 A | * | 6/1973 | Miles | 241/95 |
| 4,280,666 A | * | 7/1981 | Jones | 241/169.1 |
| 4,366,930 A | * | 1/1983 | Trombetti, Jr. | 241/169 |
| 4,397,425 A | * | 8/1983 | Moore et al. | 241/169.1 |
| 4,765,549 A | * | 8/1988 | Sherman | 241/169 |
| 5,096,128 A | * | 3/1992 | Chang | 241/56 |
| 5,618,004 A | * | 4/1997 | Klearman et al. | 241/21 |
| 5,833,928 A | * | 11/1998 | Ratajczak et al. | 422/102 |
| 6,637,684 B1 | * | 10/2003 | Ross et al. | 241/169.1 |
| 6,783,089 B2 | * | 8/2004 | Lassota | 241/30 |
| 2003/0025012 A1 | | 2/2003 | Lassota | |

* cited by examiner

*Primary Examiner*—Bena Miller
(74) *Attorney, Agent, or Firm*—Greer, Burns & Crain, Ltd.

(57) ABSTRACT

An apparatus for comminuting biological specimens includes a receiving component provided with a drive source, a sample retainer configured for retaining at least one biological specimen and for engagement in the receiving component, and a single use comminution mechanism in operational relationship with the sample retainer. The drive source is configured for driving the comminution mechanism. A collector is associated with the receiving component for receiving comminuted product generated by the comminution mechanism. A method for comminuting biological specimens is provided so that, upon comminution, the specimen is readily subject to rapid extraction and detection of drugs and their metabolites, compounds, chemicals, pesticides, steroids, growth enhancers, contaminants or other pharmacologic agents which may reside in the specimen.

13 Claims, 4 Drawing Sheets

METHOD AND APPARATUS FOR COMMINUTION OF BIOLOGICAL SPECIMENS

BACKGROUND OF THE INVENTION

The present invention is generally related to methods and apparatus for comminuting biological specimens onsite or in a laboratory, and is more particularly related to devices used for providing biological specimens for subsequent chemical analysis.

For the purposes of this application, the term "comminution" will be understood to mean to mechanically reduce to powder, pulverize, grind, shred, tear or otherwise increase the surface area of biological specimens including, but not limited to hair, feathers, nails, hooves, claws, horns, fur, beaks, scales and other sources of keratin, (or access to the cortex of the specimen), as well as bone, tissue, organs and/or muscle found in humans and animals (hereinafter referred to as biological specimens or samples), whether or not in the presence of a carrier liquid, so that the specimen is readily subject to extraction or detection of drugs and their metabolites, compounds, chemicals or other pharmacologic agents.

Increased drug abuse in North America has been associated with criminal activities, health problems, newborn addiction, lost worker productivity and staggeringly high medical costs. Currently of greatest concern are opiates (heroin, morphine, codeine), cocaine, marijuana, MDMA (Ecstasy), phencyclidine, amphetamine and methamphetamine.

Possible pesticide residues in the breast tissues of women and the concern over the presence of synthetic agents and compounds in plant and animal foodstuffs has raised concerns about possible environmental exposure including air- and water-borne agents, as well as, exposure of domestic animals to agricultural chemical agents such as pesticides and herbicides, growth hormones and/or antibiotics. Verifying a natural "organic" status prior to slaughter has, thus, recently become of significant interest.

In testing for human drugs of abuse, several test systems are presently marketed for detecting drug analytes in urine e.g., ONTRAK™ and ONLINE™ (Roche Diagnostic Systems, Inc.), the ADx™ automated fluorescence polarization immunoassay system (Abbott Laboratories, Inc.) and EZ-SCREEN™ (Environmental Diagnostics). Unfortunately, there are significant problems associated with urine testing for drugs of abuse, e.g., (i) possible false positive results for opiates recorded in subjects who are on certain medications and who have recently ingested poppy seeds; (ii) rapid elimination rates and short half-life of many drug metabolite compounds; and particularly (iii) false negatives associated with purposeful adulteration, dilution, urine substitution and other creative ways donors discover to beat a drug test.

Unlike liquid urine samples, solid samples such as hair require special sample preparation prior to conducting assays. Conceptually, hair provides a better toxicological specimen than urine, serum, sweat or saliva because its relatively slow growth increases the period of time during which drug usage is detectable. Human head hair grows approximately 1/64 (0.016) inch per day, thus creating a calendar of drug use. It takes about seven (7) days after ingestion of drugs for the drugs to be extractable from hair outside the scalp. Approximately 1.5 inches of human head hair can show drug usage over a ninety (90) day period. The hair can also be sectioned into periods of thirty (30) day use.

In present day practice, extraction of drugs from hair often involves cutting the hair it into small pieces using razor blades or scissors and inserting the cut hair into a test tube where it is then exposed to acid and/or base hydrolysis, prolonged enzymatic digestion, heat, organic solvent extraction and/or sonication. The cutting procedure is labor intensive, time consuming and is subject to the particular cutting techniques of individual technicians. Also, when multiple specimens need to be analyzed, technicians are subject to repetitive stress injuries. These methods require technical experience and are presently most easily conducted in a test laboratory. However, even then the sample process can take two to three hours to complete, and the results are not available for as long as seven days, the samples frequently suffer from poor reproducibility, there are long delays before results can be released and, even then, variability occurs in the ability to isolate different drugs and their metabolites. Hydrolysis conditions can also result in conversion of drug metabolites such as 6-monoacetylmorphine, i.e., whose presence provides judicial proof of drug abuse, into parent compounds, i.e., morphine. Fortunately, it has been found that certain drugs and their metabolites can persist in hair for extended periods of time.

Another method for preparing a sample of hair for chemical analysis is for a technician to freeze dry the sample using liquid Nitrogen, then grind the frozen hair in a mortar and pestle for 5 to 10 minutes until it is powdery in appearance. This comminution or maceration operation is useful for increasing the surface area of the hair and, thus reducing the reaction time of the analytical chemicals on the sample and increasing extractability of the agents of interest. Using this method the amount of prepared specimen obtained for analysis may vary by sample as well as by individual technician, and the liquid Nitrogen limits usage to a laboratory setting. An alternative procedure for comminution involves a ball mill, but that device inherently has contamination issues with the balls from sample to sample, and is thus only useful in a laboratory process and this method of comminution is relatively slow.

There is a need for a rapid mechanical comminution method and apparatus for biological specimens which method is easily adapted to both portable on-site comminution and laboratory comminution to prepare samples for detection of the agents of interest. There is also a need for a comminution method and apparatus for such specimens which is repeatable on an objective basis, maximizes sample integrity by eliminating cross contamination between specimens, increases the surface area of the hair and exposes the cortex of the hair for increased and rapid extractability of the agents of interest.

BRIEF SUMMARY OF THE INVENTION

The above-identified needs are met or exceeded by the present method and apparatus for the comminution of biological specimens, which provides a receiving unit and a disposable sample retainer. The preferred receiving unit is provided with a drive system for powering the comminution of the specimen and for temporarily accommodating a sample retainer. In the preferred embodiment, the sample retainer includes comminution elements which reduce the specimens to a granular or powder-like state for more efficient and rapid detection for the agents of interest. Further, the receiving unit is preferably configured for enhancing the collection of ground specimen from the sample retainer.

More specifically, an apparatus for comminuting biological specimens includes a receiving component provided with a drive source, a sample retainer configured for retaining at least one biological specimen and for engagement in the receiving component, and a single use comminution mechanism in operational relationship with the sample retainer.

The drive source is configured for driving the comminution mechanism. A collector is associated with the receiving component for receiving comminuted product generated by the comminution mechanism.

In another embodiment, a disposable sample retainer is provided for use with a comminution apparatus for comminuting a biological specimen, and includes a first portion configured for retaining the specimen and having a first comminution surface, a second portion configured for operational engagement with the first portion and having a second comminution surface, the first and second comminution surfaces being rotatable relative to each other for comminuting the specimen held therebetween.

DETAILED DESCRIPTION OF THE INVENTION

Figure 1:
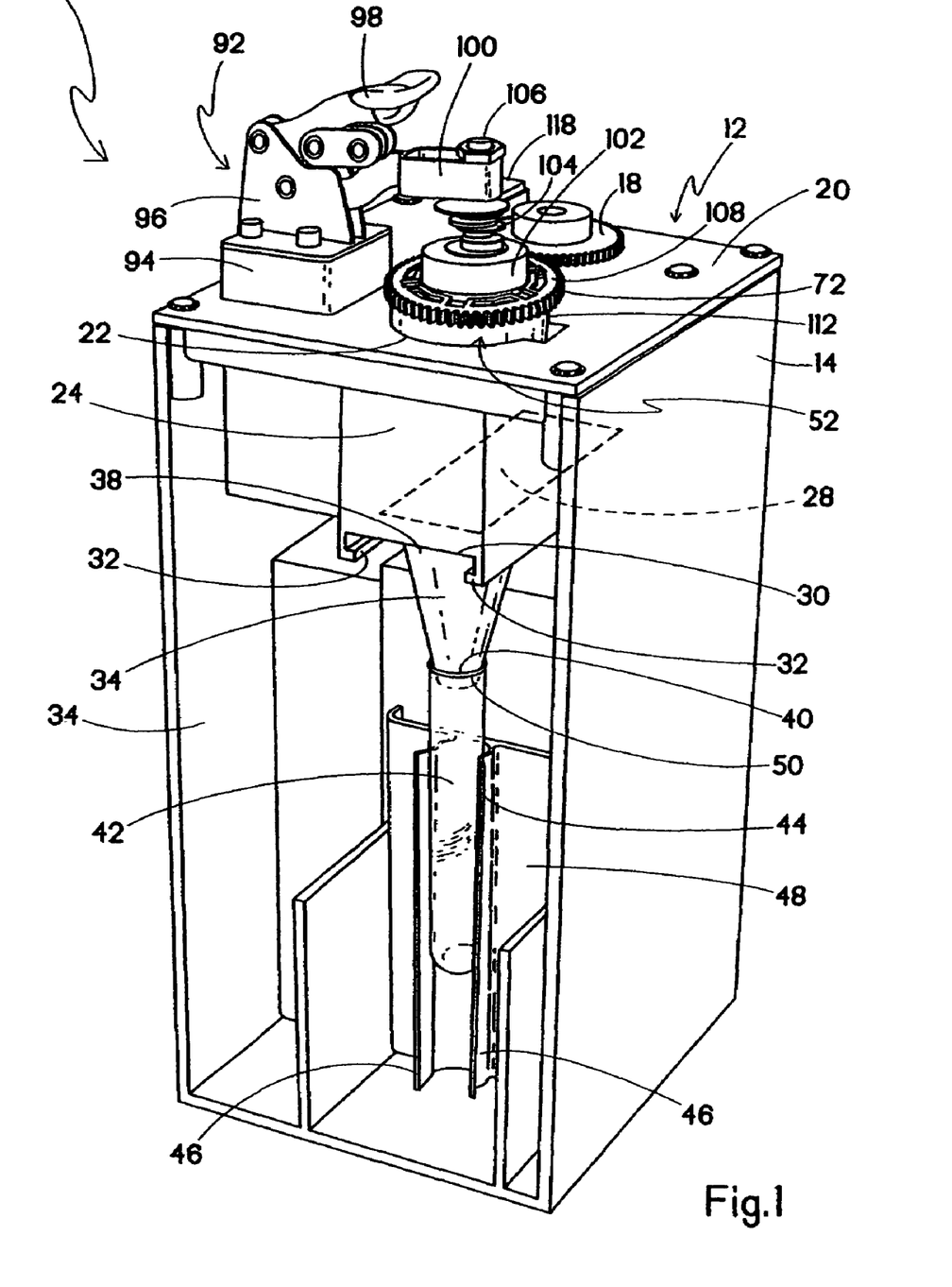
FIG. 1 is a top perspective view of the present comminution apparatus.

Referring now to FIG. 1, an apparatus or device for comminuting biological specimens or samples is generally designated 10 and is intended for comminuting specimens or samples such as hair, nails, fur, feathers, hooves or other materials having keratin, as well as other biological products such as muscle, organ and/or bone or which are known or believed to contain compounds accessible through chemical analysis and other detection systems. While the present apparatus 10 is depicted in a configuration for processing one specimen at a time, it is contemplated that the present principles of operation are convertible into an embodiment comminuting multiple specimens at a time, at least the latter having automatic control to maintain repeatability and consistency.

More specifically, the apparatus 10 includes a base unit or receiving component, generally designated 12 having a housing 14 constructed and arranged for supporting various operational components described below. In the preferred embodiment, the housing 14 is configured for placement upon a table or other work surface, and the use of terms such as "top", "bottom", "upper" and "lower" refer to the apparatus 10 as depicted in FIG. 1, however other orientations are contemplated depending on the application.

The apparatus 12 is provided with a drive source 16 preferably taking the form of an electric motor (best seen in FIG. 2), powered by either line voltage or battery power, which is located within the housing 14 so that a drive gear 18 driven by the motor is accessible. In the preferred embodiment, the drive gear 18 is disposed on a top surface 20 of the housing 14 in operational proximity to a sample well 22. The generally cylindrical sample well 22 is defined by a chamber 24 depending from the top surface 20 and being in fluid communication with an interior cavity 26, preferably through an open bottom 28.

Figure 2:
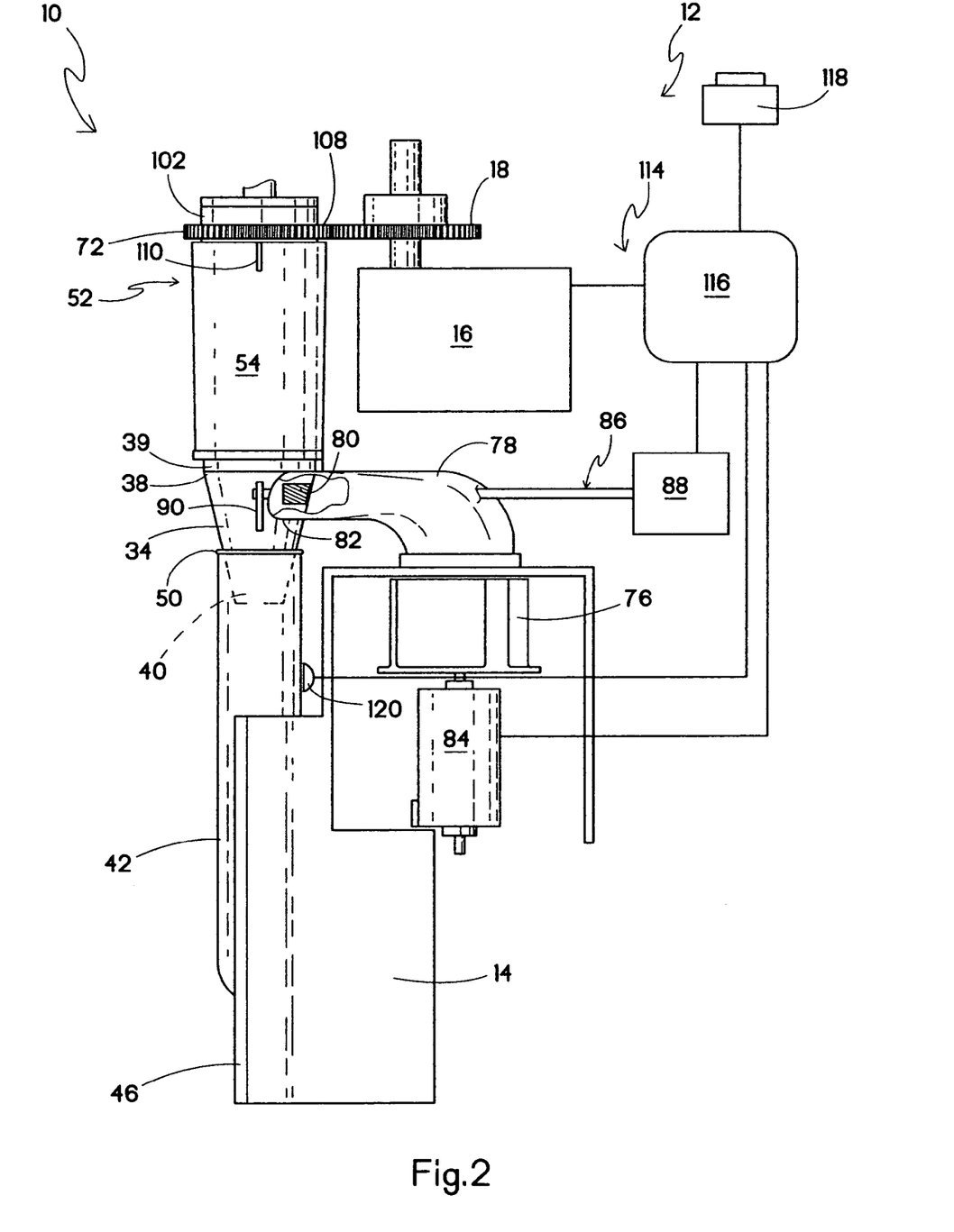
FIG. 2 is a side view of the apparatus of FIG. 1 with portions omitted for clarity.

At a lower end 30 of the chamber 24, a pair of opposing "L"-brackets 32 is disposed in generally parallel, spaced relationship to each other. The brackets 32 are configured for slidingly receiving a generally funnel-shaped filter collar 34 provided with at least one laterally extending flange 36 on an upper end 38 of the collar for slidingly engaging the brackets 32 and is generally greater in diameter than a lower end 40, which is configured for passing comminuted sample from the chamber 26 into a receiving collector 42. In the preferred embodiment, the collector 42 is at least one conventional test tube provided in a size suitable for such specimen analysis as is well known in the art. Among others, suitable test tube sizes include 12×75 mm, 10×40 mm, 13×45 mm, 13×50 mm and 13×60 mm. Alternatively, the known "Hitachi" cups are contemplated as well as other laboratory standard test tubes and other holding vessels known to those skilled in the art.

The housing 14 of the receiving component 12 is preferably configured for retaining the collector 42 in a collecting position (best seen in FIG. 1). While a variety of clamping formations, clips or brackets are contemplated, the preferred structure is a clip 44 having a generally "U"-shape when viewed in lateral section, having a pair of generally parallel spaced vertically extending arms 46. It will be appreciated that the spacing of the arms 46 is determined by the size of the desired test tube 42, and it is contemplated that the clip 44 as well as an underlying panel 48 may be exchanged for other sizes when other test tube sizes are to be used with the apparatus 10. Thus, the spacing of the arms 46 will be sufficient to provide a slight yet positive gripping force on the test tube 42 without causing damage. It is also contemplated that the lower end 40 of the filter collar 34 will fit inside an upper end 50 of the test tube 42.

Figures 3, 3A:
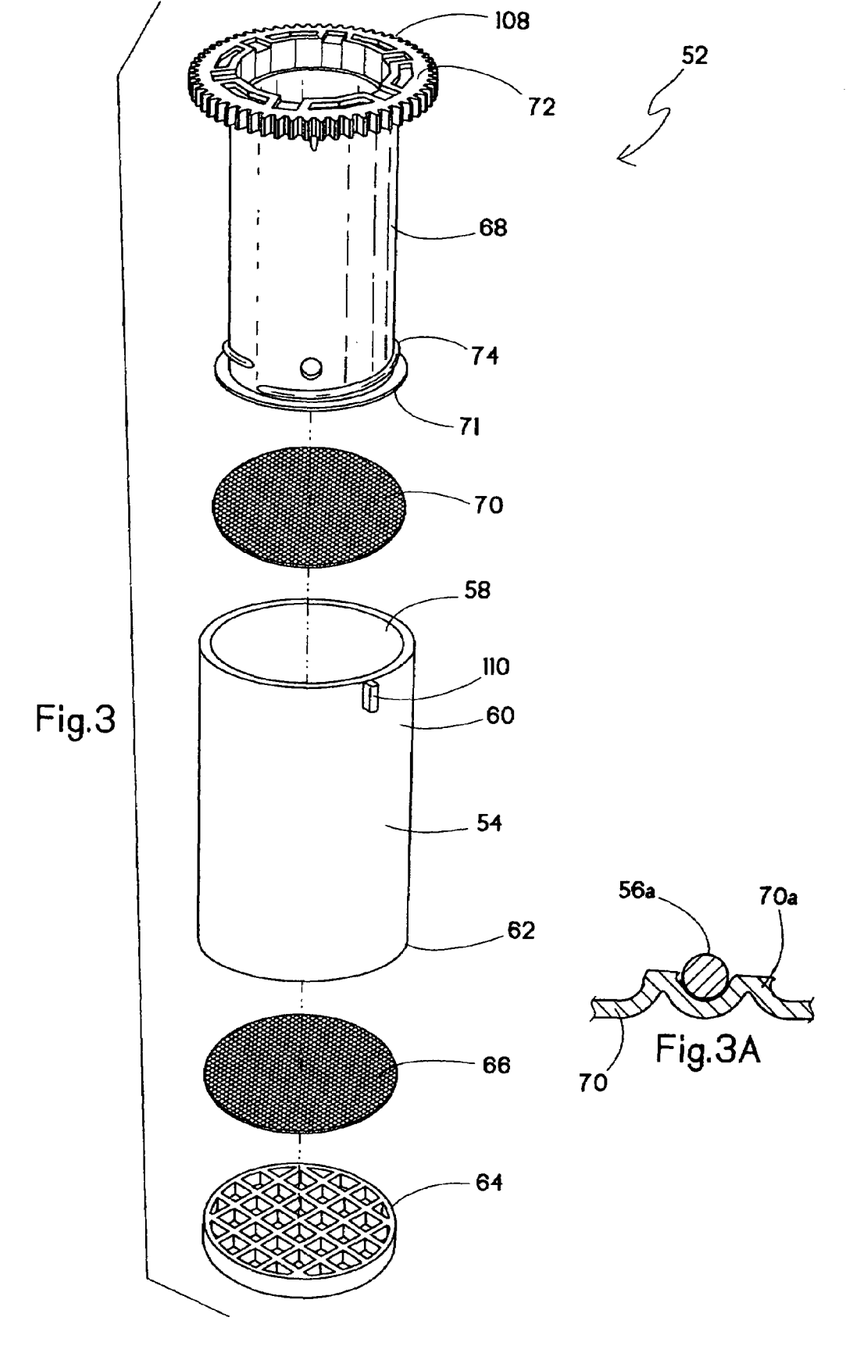
FIG. 3 is an exploded perspective view of the sample retainer apparatus of FIG. 1.
FIG. 3A is a fragmentary enlarged section of a second comminution surface.
Figure 4:
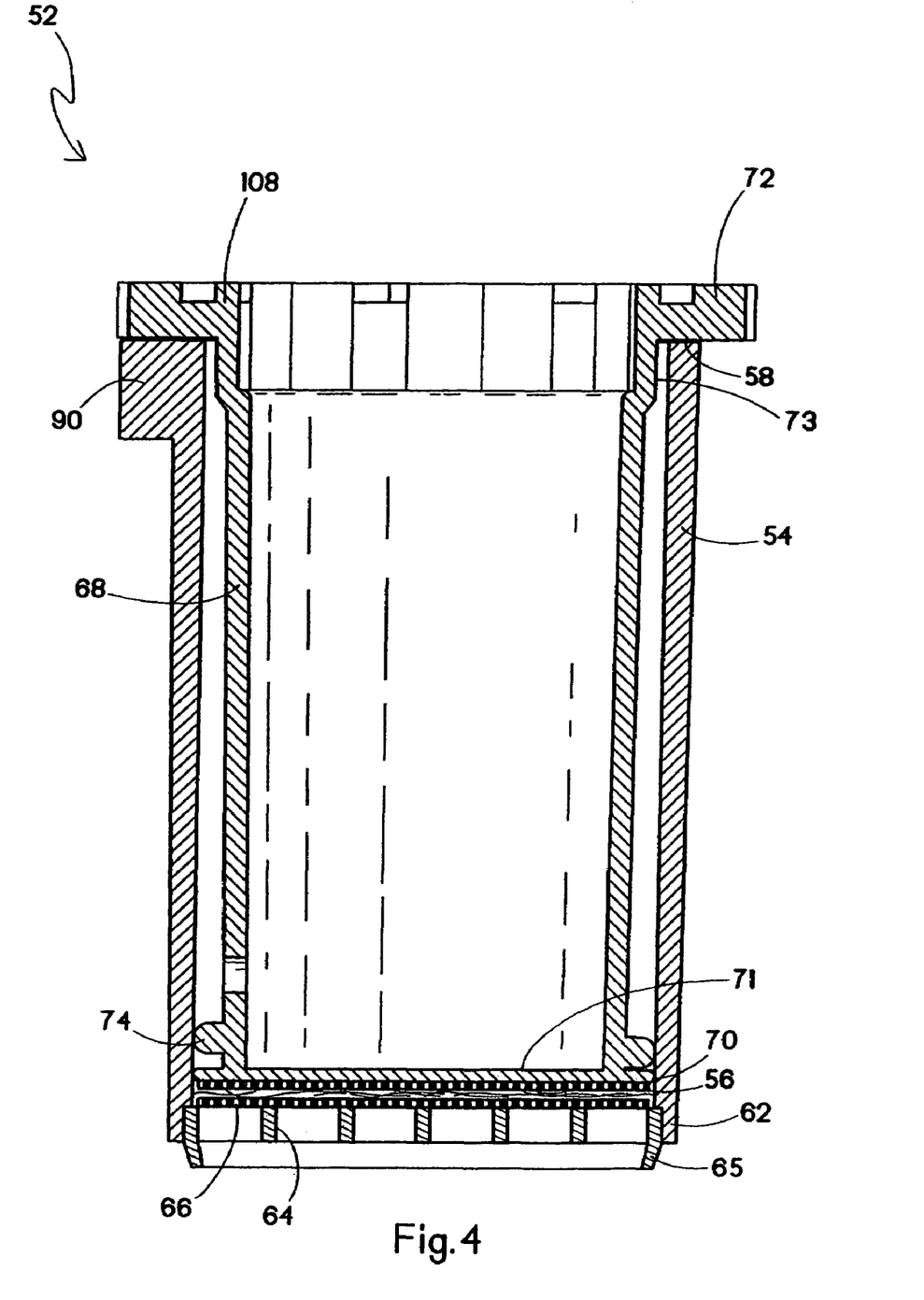
FIG. 4 is a vertical section of an assembled view of the sample retaining apparatus of FIG. 3.

Referring now to FIGS. 3 and 4, an important portion of the comminution apparatus 10 is a sample retainer, generally designated 52, configured both for retaining at least one biological specimen and for engagement in the sample well 22 of the receiving component 12. The sample retainer 52 is operationally associated with a single use comminution mechanism configured for converting a raw specimen into a granular or powdery product more amenable to chemical analysis and other detection systems. In the preferred embodiment, this comminution is obtained by relative rotation of a first component of the sample retainer relative to a second component. This relative rotation is powered by the driving source 16. The comminuted sample is received in the filter collar 34 and ultimately in the collector or test tube 42. It is contemplated that the receiving component 12 may alternately have a separate single use comminution mechanism separate from the sample retainer.

More specifically, in the embodiment of FIGS. 3 and 4 the sample retainer 52, also referred in some cases as "a consumable" since it is designed for single use, includes a first component referred to as a cup 54 configured for retaining the above-identified sample or biological specimen 56, which may be obtained from a variety of human and animal products. In the preferred embodiment, the sample 56 is depicted as a group of hair fibers cut to an approximate 1.5 inch length and having a weight of approximately 20 mg, which, when the hair is taken from the head, represents about 90 days of potential drug use. It is preferred that about 10-20 hairs are suitable as the sample 56. However, it is contemplated that the size of the sample 56 may vary with the application and/or with the type of hair collected or the location on the body from which the specimen is collected.

The dimensions of the sample retainer 52 are chosen based on the desired sample size. The cup 54 is generally cylindrical in shape, with an open upper end 58 defined by a generally tubular sidewall 60. While other lengths and aspect ratios are contemplated, the present sidewall is at least approximately 1.5 inches in length and about 0.875 inch in diameter to adequately accommodate the sample 56.

Opposite the upper end 58 is a lower end 62 provided with a supportive grid 64. The grid 64 consists of first and second pluralities of spaced bars oriented normally to each other. As a result, a supportive yet porous surface is obtained. The grid 64 is secured to the lower end 62 either by being integrally molded to the sidewall 60 or held there by chemical adhesive, ultrasonic welding or similar fastening techniques. To enhance the retention of comminuted particles of the sample 56, the grid 64 is preferably provided with a transition formation 65 preferably in the form of a depending, annular tapered lip configured for insertion into the upper end 38 of the collar 34.

Atop the grid 64 is secured at least one first comminution surface 66 provided in the form of a generally planar perforated metal disk. In the preferred embodiment, the disk 66 is made from, or using techniques known in the electric shaver art for producing electric shaver foil having apertures in the approximate range of 0.025 inch, however the size and shape of the openings in the disk may vary to suit the application, provided they are large enough to pass comminuted hair fibers therethrough. Human hair fibers typically have a diameter in the range of 0.002-0.004 inch. Another desirable property of the disk 66 is that it is designed to serve as a fixed surface or "anvil" and as such is perforated but has a generally level upper surface. In the preferred embodiment, this surface is produced by electroplating or electrodeposition. The disk 66 is preferably secured to the grid 64 by chemical adhesive, ultrasonic welding, insert molding or similar fastening technology.

While a shaver foil or similar perforated disk is the preferred material and construction for the comminution surface 66, it is contemplated that other materials would be suitable provided they produce comminuted hair, feathers, nails, hooves, horns, fur, beaks, and other sources of keratin or other specimens found in humans and animals suitable for chemical analysis and other detection systems. It is also contemplated that the comminution surface 66 may be integrally formed with the grid 64 and even be made of the same material.

A second component of the sample retainer 52 is referred to as a ram 68 and is configured for operational engagement with the cup 54 and having at least one second comminution surface 70. The ram 68 pushes the sample 56 toward the first comminution surface 66 and maintains the sample there until comminution is complete. Another function of the ram 68 is to provide the second comminution surface 70, which acts against the first surface 66 to comminute the sample 56. Since the comminution process is obtained through relative rotation of the first and second surfaces 66, 70 in the preferred embodiment the ram 68 is configured for being rotated by the motor 16, and as such functionally serves as the "hammer" of the two comminution surfaces 66, 70. In a similar fashion to the attachment of the first comminution surface 66 to the cup 54, the second comminution surface 70 is attached to a corresponding surface 71 of the ram 68 by chemical adhesive, ultrasonic welding, insert molding, or integral manufacturing with the ram as is known in the art.

Referring now to FIGS. 3 and 3A, the disk 70 is secured to the ram 68 as described above to provide sufficient abrasive force when the surfaces 66, 70 are rotated against each other to comminute strands of hair into a granular or powdery consistency. In the preferred embodiment, the disk 70 is preferably made of metal by stamping to form a bossed or dimpled, generally planar surface. The sharpness of the edges of the bosses 70a may be enhanced by subsequent grinding or lapping operations. It has been found that, for desired results when human hair is being comminuted, the height of the bosses 70a should be less than the diameter of the thickness of the hair strands 56a. Thus, in the preferred embodiment, the bosses 70a have a height of approximately 0.002-0.0025 inch. It is contemplated that the boss height may vary to suit the application or the sample type and size, and that boss height may vary within or upon the same surface 70.

While shaver foil is the preferred material for the surface 70, and while the comminution apparatus is presently disclosed in the form of opposed comminution surfaces 66, 70, other comminution surfaces or apparatus capable of comminuting hair, feathers, nails, hooves, horns, fur, beaks, and other sources of keratin or other types of specimens found in humans and animals are contemplated. For example, it is contemplated that the surfaces 66, 70 may be made of other materials, including metals such as stainless steel, nickel, aluminum alloys of the above and similar metals, plastics, abrasives such as sandpaper, silica carbide or other suitable abrasive or grinding materials. It is further contemplated that the foil surfaces 66, 70 may be exchanged on the respective cup 54 and ram 68 and also that the cup may rotate relative to the ram.

Since the ram 68 is movable relative to the cup 54, it is provided with a gear 72 or equivalent drive formation opposite the comminution surface 70. In the preferred embodiment, the gear 72 is integrally molded to the ram 68 and is provided with a radially extending tooth configuration which meshes with the drive gear 18. The precise tooth pattern may vary to suit the application as is known in the art. As the ram 68 rotates relative to the cup 54, a radially extending bearing surface 73 located beneath the gear 72 slidably engages the inner sidewall 60 for maintaining proper alignment of the ram in the cup, and also for maintaining proper engagement of the gears 72, 18.

Another feature of the ram is that it is preferably configured for retaining the sample 56 between the surfaces 66, 70. To that end, the ram 68 is provided with a sample retainer formation 74 for retaining the sample in place during comminution. It has been found that sample portions often creep upward away from the surfaces 66, 70. The present sample retainer formation 74 is preferably formed as a radially extending helical rib which prevents the sample 56 from migrating away from the surfaces 66, 70 by forming a downward directing, moving barrier which acts like an auger against an inner surface of the cup 54 and rotates with the ram 68. When provided as a helical rib, the formation 74 has to be oriented to accommodate the direction of rotation of the ram 68 to push the stray hair towards the comminution surfaces, 66, 70. Through the use of the retainer formation 74, the sample is maintained in operational relationship to the comminution surfaces 66, 70.

An important feature of the present sample retainer 52 is that it is disposable to facilitate single use and avoid cross contamination of samples. Accordingly, the cup 54 and the ram 68 are configured for easy detachability from the sample well 22. In the preferred embodiment, the sample retainer 52 is vertically removable from the well 22, however other disengagement configurations are contemplated. With the preferred configuration, when the sample retainer 52 is removed, the comminution surfaces 66, 70 as well as the drive formation 72 and the retainer formation 74 are also removed, those being the surfaces subject to contact with the sample 56, before and after comminution. In addition, the cup 54 and the ram 68 are made of relatively inexpensive materials, which may include an anti static property. Alternatively, the cup 54 and/or the ram 68 may be made of material or otherwise equipped to neutralize positive or negative charges in the sample 56 or the cup 54.

Referring now to FIG. 2, once the sample 56 is placed between the surfaces 66, 70 and there is resulting relative rotation by the drive source 16 for a specified period of time, the comminuted sample passes through the apertures in the surface 66, through the supportive grid 64 and into the filter collar 34. It has been found that in some situations, the comminuted sample does not fall freely into the filter collar 34 and ultimately into the collector 42. As such, the receiving component 12 is preferably provided with at least one flow enhancer 76. In the preferred embodiment, one flow enhancer 76 is a vacuum fan (FIG. 2) which creates a negative pressure at the filter collar 34 by drawing air flow through an elbow duct 78 located within the receiving component 12 and which is in fluid communication with the filter collar.

Air flows through the filter collar 34 in a generally lateral direction by virtue of a porous filter screen 80 (FIG. 2) affixed in an opening in a wall-of the filter collar. The ram 68 is preferably provided with at least one air vent 81 for facilitating the flow of air through the sample retainer 52. Alternatively, air may flow through the collar 34 and the cup 54 through a filter at the bottom of the cup. A mesh size is selected for the filter screen 80 so that air flows through, but comminuted bits of sample 56 are caught on the screen. Other types of filter material may be used as well to separate grades of comminuted particles as to size. In instances where there is a need for enhanced retention of the volume of comminuted sample, a motor 84 powering the vacuum fan 76 may be intermittently energized, instead of being constantly energized. It is believed that intermittent energization will enhance retention of comminuted sample 56.

The filter collar 34 is mounted in the receiving component 12 so that the filter screen 80 is in communication with the duct 78. To provide adequate suction generated by the fan 76, the duct 78 has a collar end 82 (shown partially cut away) configured for tightly engaging the conical wall of the filter collar 34.

It is also contemplated that a second flow enhancer is provided, designated 86. In the preferred embodiment, the second flow enhancer 86 is a vibrator, which generates pulse impacts against the filter collar 34 to facilitate the downward flow of comminuted sample 56 into the collector 42. More specifically, the vibrator 86 in one embodiment includes a motor 88 powering an eccentric cam 90 which is in periodic contact with the filter collar 34. Other configurations and orientations of vibrating mechanisms are contemplated, provided the flow of comminuted sample is enhanced.

Referring now to FIGS. 1 and 2, for beneficial results, it is preferable that there be a biasing force exerted against the sample retainer 52 so that the respective comminution surfaces 66, 70 exert sufficient pressure against the sample 56 to achieve desirable comminution. Accordingly, the receiving component 12 is provided with least one biasing device 92 configured for exerting a biasing force on the sample retainer 52. The preferred biasing device 92 is a releasable clamp affixed at a base 94 to the top surface 20 of the receiving component 12.

An over center lever/cam apparatus 96 is secured to the base 94 and includes a handle 98 and an actuator arm 100. At a free end of the actuator arm 100, a rotatable contact pad 102 is secured and is biased vertically by a spring 104. The amount of spring force exerted by the contact pad 102 is determined by a threaded adjustment of an attachment rod 106. When the handle 98 is pressed in a downward position (FIG. 1), the actuator arm 100 is fixed in a lowered position with the contact pad 102 impacting an end 108 of the ram 68 having the gear 72. Thus, the contact pad 102 exerts a vertical biasing force against the ram 68, forcing the comminution surface 70 against the comminution surface 66 in the cup 54. Further, the contact pad 102 rotates with the ram 68. It has been found that about 5 pounds of force provides suitable results, but other degrees of biasing force are contemplated depending on the application.

In the biased position shown in FIG. 1, the gear 72 is meshed with the drive gear 18. It is contemplated that the contact pad 102 rotates with the ram 68 when the drive gear is driving the ram to effect comminution. Upon completion of the comminution process, the handle 98 is pulled upward to release the biasing force on the ram. At that point, the sample retainer. 52 may be withdrawn from the receiving component 12.

As the ram 68 rotates relative to the cup 54, the cup is held stationary or prevented from rotation by being keyed to the sample well 22. At least one radially projecting lug 110 on the cup 54 is received in a corresponding slot 112 in the sample well 22. Upon vertical insertion of the sample retainer 52 into the sample well 22, the lug 110 is engaged in the slot 112 to properly seat the sample retainer.

Referring now to FIG. 2, control over the comminution operation is maintained by a control circuit 114 shown schematically. The circuit 114 includes a microprocessor 116, programmable controller, central processing unit or similar device, and is actuated by an actuator 118, represented by a start switch located on the receiving component 12. The microprocessor 116 is connected to the drive motor 16, the vacuum fan motor 84, the eccentric vibrator motor 88 if included and other automated functions of the apparatus 10. As is well known in the art, actuation of the switch 118 is configured for individually and cooperatively controlling the operation of the drive motor 16 as well as the vacuum fan motor 84 and the vibrator motor 88 if included. It is contemplated that the various motors 16, 84 and 88 may be operated sequentially for facilitating the comminution and collection of comminuted sample 56.

For automatic operation of the apparatus 10, it is helpful to be able to monitor the condition of the comminuted sample 56 once it reaches the collector 42. Many chemical analyses performed on comminuted samples 56 such as human hair are dependent upon the weight of the comminuted sample. Also, when multiple samples 56 are comminuted at a time, a more automated apparatus is preferred for saving time as well as for maintaining consistency and repeatability of the process. Accordingly, the microprocessor 116 is preferably connected to a sensor 120 in operational proximity to the collector 42. The sensor 120 is schematically represented, since it is contemplated that the sensor may monitor various properties of the comminuted sample 56 including, but not limited to weight, height in the collector 42, particle size, volume and opacity. Appropriate types of sensors 120 for monitoring such properties include infrared, mechanical, scales, optical and electronic types as are known in the art. Once connected to the microprocessor 116, the sensor 120 provides feedback information in the form of signals which, when sent to the microprocessor, trigger predetermined operational cycles of the motors, 16, 84 and 88 as desired. For example, upon reaching a predetermined weight of sample in the collector 42, the main drive motor 16 is turned off to stop the comminution process.

Also, while only one sample retainer 52 and associated receiving portion 12 are discussed, it is contemplated that a unit incorporating the above-described principles of operation may be provided with the capability of simultaneously processing multiple samples at a time. The receiving portion 12 may be provided in a format suitable for processing single or small volumes of sample retainers 52, or large volumes of such retainers. In the latter applications it is contemplated that the functions of driving the gear 72 on the ram 68, exerting the biasing force to facilitate comminution and initiating the vacuum may be performed by the master control circuit 114 operating on multiples of the components described above. Also, it is contemplated that the microprocessor 116 may be programmed for varying the time of comminution, vacuum and/or vibration as a function of the size of the sample 56.

It is also contemplated that replacement kits of consumables be provided to users of the receiving component 12 or similar device. Such a kit would include at least a cup 54 with the grid 64 and the first comminution surface 66, a ram 68 with the second comminution surface 70. In addition, the kit would preferably include a filter collar 34 and a collector or test tube 42. Thus, any of the components coming in contact with the specimen are single use and disposable.

In operation, the present invention also contemplates the following method of comminuting specimens or samples for obtaining subject matter upon which chemical analysis may be performed. While the method is preferably performed with the apparatus described above, it is contemplated that other apparatus may be provided for achieving the same goals of generating comminuted sample material suitable for chemical testing and other detection systems.

More specifically, the method includes first providing a biological sample comminution device including the receiving component 12 provided with the drive source 16, the sample retainer 52 configured for retaining at least one biological specimen 56 and for engagement in the receiving component 12, the sample retainer associated with a single use comminution mechanism 66, 70, the drive source configured for driving the comminution mechanism and a collector 42 associated with the receiving component for receiving comminuted product generated by the comminution apparatus 10. Next, the filter collar 34 is loaded into the receiving component 12, after which the collector 42 is also loaded onto the component.

As an option, the biological sample 56 is prewashed while in the first component 54 with methanol or other suitable liquids or compounds, and possibly subject to sonication or agitation, for removing external substances from the sample which may skew the results of the analysis. A removable filter material or screen may be placed at the bottom of the first component or cup 54 to prevent pre-wash movement of the sample through the foil during the washing period, and then removed before the second component 68 is engaged. The biological sample 56 is then placed into the first component 54 of the sample retainer 52, and the first component is then loaded into the receiving device.

It has been found that the samples of hair are awkward to handle and are difficult to position suitably at the bottom of the cup 54. The preferred orientation, in the case of human hair, is flat or generally coplanar with the first comminution disk surface 66. It has been found that if the hair is moistened with methanol it is easier to locate in the cup 54. The methanol holds the hair together in a temporary bond which is released as the liquid evaporates. Also, the ethanol or methanol or other liquids quickly vaporizes without residue, especially when vacuum is used. Alternately, tweezers, cardboard or otherwise disposable plungers, or a technician's finger may be used for placing the sample.

The source of vacuum 84 is then turned on for drawing air through the sample retainer to dry the sample. After the sample is dry, the second component 68 of the sample retainer 52 is engaged with the first component of the sample retainer with the biological sample 56 therebetween. A biasing force is exerted against the first component 54 of the sample retainer 52 so that the first comminution surface 66 on the first component engages the second comminution surface 70 on the second component 68, and the drive source 16 is initiated to rotate the second component relative to the first component 54 to cause comminution of the specimen within the retainer 52. Using the microprocessor 116, with or without the sensor 120, the operation of the drive source 16 may be varied as to time of operation, direction of rotation and/or intermittent or constant rotation. If desired, vacuum and/or vibration are employed by controlling the motors 84, 88 to facilitate movement of comminuted sample into the collector 42.

It will be seen that the present sample comminution apparatus 10 more efficiently provides comminuted sample for subsequent chemical analysis and other detection systems. It has been found that a typical 20 mg sample of hair requires about 2 to 5 minutes of comminution to reach a sufficiently comminuted consistency for chemical analysis and other detection systems. Using the present system, the process of comminution and chemical extraction has been reduced from several hours to about 30 minutes, and can be performed onsite rather than in a remote laboratory. Samples produced according to the present invention have been found to provide higher recovery in a shorter period of time in the subsequent chemical analysis than samples prepared according to prior techniques. The present system for comminuting hair samples has been found to expose the hair's cortex to enhance the reactivity of the hair with the analytical chemicals and other detection systems.

While specific embodiments of the present method and apparatus for the comminution of biological specimens has been shown and described, it will be appreciated by those skilled in the art that changes and modifications may be made thereto without departing from the invention in its broader aspects and as set forth in the following claims.

What is claimed is:

1. A disposable sample retainer for use with a comminution apparatus for comminuting a biological specimen consisting of strands of hair, comprising:

a first portion configured for retaining the specimen and having a first generally planar comminution surface and a planar support grid separately formed from said first comminution surface and configured for being at least partially received within said first portion, said grid provides a supportive yet porous surface across said first comminution surface where the specimen is retained;

a second portion configured for operational engagement with said first portion and having a second generally planar comminution surface;

said first and second comminution surfaces being rotatable relative to each other for comminuting the specimen held therebetween;

said first comminution surface being located below said second surface, said first surface being porous and said grid having multiple apertures for permitting the passage of the comminuted specimen;

wherein said second comminution surface is provided with a plurality of spaced bosses having a height which is less than a diameter of strands of the specimen, said bosses being provided with sharpened edges so that upon relative rotation of said first and second surfaces, the strands of hair will be comminuted into a granular or powdery consistency; and wherein said first portion is a cup configured for retaining the specimen, and said second portion is a ram configured for operational engagement with said cup and having said generally planar comminution surface, said ram configured for rotating relative to said cup for effecting said comminution.

2. The sample retainer of claim 1 wherein said first portion has said support grid at one end.

3. The sample retainer of claim 2 wherein said first comminution surface is disposed above said grid.

4. The sample retainer of claim 1 wherein said second portion is a ram having a drive formation at one end and said second comminution surface at an opposite end.

5. The sample retainer of claim 4 wherein said ram is provided with a sample retainer formation for retaining the specimen in operational relation to said first and second comminution surfaces.

6. The sample retainer of claim 5 wherein said sample retainer formation is helically shaped, extends radially from said ram and rotates with said ram relative to said first portion free of threaded engagement with said first portion.

7. The sample retainer of claim 1 wherein said second portion is provided with a gear as a drive engagement formation for rotation relative to said first portion.

8. The sample retainer of claim 1 further including at least one filter collar configured for operational association with a lower surface of said first portion for receiving comminuted sample generated by the relative rotation of said first and second comminution surfaces and passing through said first comminution surface, said filter collar having an open lower end for permitting passage of comminuted sample therethrough.

9. The sample retainer of claim 1 further including a transition formation associated with said sample retainer for facilitating the flow of comminuted specimen from said porous lower end to a collector.

10. The sample retainer of claim 1 wherein said first and second portions are configured so that said comminution and relative rotation occurs independent of attachment of said first portion to said second portion.

11. The sample retainer of claim 1, wherein upon assembly of said first portion to said second portion, an upper end of said second portion engages said first portion for determining a separation distance between said respective comminution surfaces.

12. A disposable sample retainer for use with a comminution apparatus for comminuting a biological specimen, comprising:
a first portion configured for retaining the specimen and having a first planar comminution surface;
a second portion configured for operational engagement with said first portion and having a second planar comminution surface;
said first and second comminution surfaces being rotatable relative to each other for comminuting the specimen held therebetween, one of said first and second portions having a drive engagement formation configured for being driven relative to the other said portion by a drive motor;
said first comminution surface being located below said second surface, said first surface being porous for permitting the passage of the comminuted specimen;
said first and second portions being configured so that the specimen is enclosed within the sample retainer prior to comminution, during comminution said specimen partially passes through said porous first surface, and at the conclusion of comminution said specimen is fully comminuted and falls through said porous first surface;
wherein the specimen to be comminuted is strands of hair, and one of said first and second surfaces is provided with a plurality of spaced, sharp-edged bosses constructed and arranged for comminuting the strands of hair to a granular or powdery consistency.

13. A disposable sample retainer for use with a comminution apparatus for comminuting a biological specimen, comprising:
a first portion configured for retaining the specimen and having a first planar comminution surface and a planar support grid separately formed from said first planar comminution surface and configured for being at least partially received within said first portion, said grid provides a supportive yet porous surface across said first comminution surface where the specimen is retained;
a second portion configured for operational engagement with said first portion and having a second planar comminution surface;
said first and second comminution surfaces being rotatable relative to each other for comminuting the specimen held therebetween;
said first comminution surface being located below said second surface, said first surface being porous and said grid having multiple apertures for permitting the passage of the comminuted specimen;
said second portion is a ram having a drive formation at one end and said second comminution surface at an opposite end, said ram is provided with a sample retainer formation for retaining the specimen in operational relation to said first and second comminution surfaces; and
said sample retainer formation is helically shaped, extends radially from said ram and rotates with said ram relative to said first portion free of threaded engagement with said first portion.

* * * * *